US012655266B2

(12) United States Patent
Park et al.

(10) Patent No.: US 12,655,266 B2
(45) Date of Patent: *Jun. 16, 2026

(54) MONOMER COMPOSITION FOR SYNTHESIZING RECYCLED PLASTIC, PREPARATION METHOD THEREOF, RECYCLED PLASTIC, AND MOLDED PRODUCT USING THE SAME

(71) Applicant: LG CHEM, LTD., Seoul (KR)

(72) Inventors: Eunju Park, Daejeon (KR); Ki Jae Lee, Daejeon (KR); Jungmoon Bae, Daejeon (KR); Jeongbin Lee, Daejeon (KR); Mooho Hong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 600 days.

This patent is subject to a terminal disclaimer.

(21) Appl. No.: 18/032,117

(22) PCT Filed: Jul. 14, 2022

(86) PCT No.: PCT/KR2022/010315
§ 371 (c)(1),
(2) Date: Apr. 14, 2023

(87) PCT Pub. No.: WO2023/038270
PCT Pub. Date: Mar. 16, 2023

(65) Prior Publication Data
US 2023/0374251 A1     Nov. 23, 2023

(30) Foreign Application Priority Data

Sep. 13, 2021     (KR) ........................ 10-2021-0122001
Sep. 13, 2021     (KR) ........................ 10-2021-0122002
Sep. 13, 2021     (KR) ........................ 10-2021-0122003
Sep. 13, 2021     (KR) ........................ 10-2021-0122004
Sep. 29, 2021     (KR) ........................ 10-2021-0128892
Oct. 13, 2021     (KR) ........................ 10-2021-0136153

(51) Int. Cl.
| | |
|---|---|
| *C08G 64/06* | (2006.01) |
| *C07C 37/01* | (2006.01) |
| *C07C 37/055* | (2006.01) |
| *C07C 37/52* | (2006.01) |
| *C07C 37/68* | (2006.01) |
| *C07C 37/80* | (2006.01) |
| *C07C 37/82* | (2006.01) |
| *C07C 37/86* | (2006.01) |
| *C07C 39/16* | (2006.01) |
| *C08G 64/16* | (2006.01) |
| *C08J 11/16* | (2006.01) |
| *C08J 11/24* | (2006.01) |
| *C08L 69/00* | (2006.01) |

(52) U.S. Cl.
CPC .............. *C08J 11/24* (2013.01); *C07C 37/01* (2013.01); *C07C 37/0555* (2013.01); *C07C 37/52* (2013.01); *C07C 37/685* (2013.01);

*C07C 37/80* (2013.01); *C07C 37/82* (2013.01); *C07C 37/86* (2013.01); *C07C 39/16* (2013.01); *C08G 64/06* (2013.01); *C08G 64/16* (2013.01); *C08J 11/16* (2013.01); *C08L 69/00* (2013.01); *C08J 2369/00* (2013.01); *C08L 2207/20* (2013.01)

(58) Field of Classification Search
USPC ........................................................ 521/40
See application file for complete search history.

(56) References Cited

U.S. PATENT DOCUMENTS

| | | | |
|---|---|---|---|
| 4,843,733 | A | 7/1989 | Admassu |
| 5,652,275 | A | 7/1997 | Buysch et al. |
| 5,675,044 | A | 10/1997 | Eijsbouts et al. |
| 8,680,226 | B1 | 3/2014 | Bell et al. |
| 8,680,227 | B1 | 3/2014 | Bell et al. |
| 2004/0054238 | A1 | 3/2004 | Ban et al. |
| 2008/0194713 | A1 | 8/2008 | Kim et al. |
| 2009/0170969 | A1 | 7/2009 | Ogasawara |
| 2011/0009592 | A1 | 1/2011 | Ooms et al. |
| 2012/0248038 | A1 | 10/2012 | Fritz et al. |
| 2014/0179892 | A1 | 6/2014 | Bell et al. |
| 2015/0105531 | A1 | 4/2015 | Stanislaus et al. |
| 2015/0291763 | A1 | 10/2015 | Bell et al. |
| 2016/0168063 | A1 | 6/2016 | Stanislaus et al. |

FOREIGN PATENT DOCUMENTS

| | | |
|---|---|---|
| CN | 1179438 A | 4/1998 |
| CN | 1233625 A | 11/1999 |
| CN | 1481347 A | 3/2004 |
| CN | 101166705 A | 4/2008 |
| CN | 101407450 A | 4/2009 |
| CN | 101942080 A | 1/2011 |
| CN | 104718238 A | 6/2015 |

(Continued)

OTHER PUBLICATIONS

KR20080008333 Machine Translation (Year: 2008).*
KR20150028359-A Machine Translation (Year: 2015).*
Quaranta et al., (2017), "Depolymerization of Poly(bisphenol A carbonate) Under Mild Conditions By Solvent-Free Alcoholysis Catalyzed by 1,8-diazabicyclo[5.4.0]undec-7-ene As a Recyclable Organocatalyst: A Route To Chemical Recycling of Waste Polycarbonate," Green Chemistry, vol. 19, Issue 22, pp. 5422-5434.
Jie, et al., (2006), "Study on Depolymerization of Polycarbonate in Supercritical Ethanol," Polymer Degradation and Stability, vol. 91, Issue 10, Elsevier, pp. 2307-2314.
Research on the Alcoholization and Recovery of Bisphenol A and Dialkyl Carbonate from Waste Polycarbonate Materials, Chai Fangjun, China excellent masters dissertation full text database, Engineering and Technology I, (English abstract provided) 85 pages, Jun. 2013.

(Continued)

*Primary Examiner* — Terressa Boykin

(74) *Attorney, Agent, or Firm* — Bryan Cave Leighton Paisner LLP

(57) ABSTRACT

The present disclosure relates to a monomer composition for synthesizing recycled plastic that contains a high-purity aromatic diol compound recovered through recycling by chemical decomposition of a polycarbonate-based resin, a method for preparing the same, and a recycled plastic and molded product using the same.

13 Claims, No Drawings

(56) References Cited

FOREIGN PATENT DOCUMENTS

| | | | | | | |
|----|----------------|----|---------|---|---|----------|
| CN | 105658712 | A | 6/2016 | | | |
| CN | 111484395 | A | 8/2020 | | | |
| CN | 116583495 | A | 8/2023 | | | |
| EP | 1873135 | A1 | 1/2008 | | | |
| EP | 0662101 | B1 | 5/2009 | | | |
| EP | 4253356 | A1 | 10/2023 | | | |
| EP | 4345127 | A1 | 4/2024 | | | |
| EP | 4365224 | A1 | 5/2024 | | | |
| JP | 40-16536 | | 7/1965 | | | |
| JP | H02-504125 | A | 11/1990 | | | |
| JP | 1995-025798 | A | 1/1995 | | | |
| JP | 1995-196582 | A | 8/1995 | | | |
| JP | H10-087540 | A | 4/1998 | | | |
| JP | 1998-259151 | A | 9/1998 | | | |
| JP | H10-259151 | A | 9/1998 | | | |
| JP | 2000-256242 | A | 9/2000 | | | |
| JP | 2001-192497 | A | 7/2001 | | | |
| JP | 2001-270961 | A | 10/2001 | | | |
| JP | 3290054 | B2 | 6/2002 | | | |
| JP | 2002-265798 | A | 9/2002 | | | |
| JP | 2003-041049 | A | 2/2003 | | | |
| JP | 3422647 | B2 | 6/2003 | | | |
| JP | 2004-277396 | A | 10/2004 | | | |
| JP | 2004-339340 | A | 12/2004 | | | |
| JP | 2005-162674 | A | 6/2005 | | | |
| JP | 2005-162675 | A | 6/2005 | | | |
| JP | 2005-179228 | A | 7/2005 | | | |
| JP | 2005179460 | A | 7/2005 | | | |
| JP | 2006-022183 | A | 1/2006 | | | |
| JP | 2006-045129 | A | 2/2006 | | | |
| JP | 2006052174 | A | 2/2006 | | | |
| JP | 4116533 | B2 | 7/2008 | | | |
| JP | 4323395 | B2 | 9/2009 | | | |
| JP | 4575074 | B2 | 11/2010 | | | |
| JP | 4575082 | B2 | 11/2010 | | | |
| JP | 2011-195514 | A | 10/2011 | | | |
| JP | 5435538 | B2 | 3/2014 | | | |
| JP | 5704736 | B1 | 4/2015 | | | |
| JP | 2015-535854 | A | 12/2015 | | | |
| JP | 2016-505591 | A | 2/2016 | | | |
| JP | 5985757 | B2 | 9/2016 | | | |
| JP | 2016-533416 | A | 10/2016 | | | |
| JP | 2016204265 | A | 12/2016 | | | |
| JP | 2017-052892 | A | 3/2017 | | | |
| JP | 2017095379 | A | 6/2017 | | | |
| KR | 10-2004-0055726 | A | 6/2004 | | | |
| KR | 10-2005-0098385 | A | 10/2005 | | | |
| KR | 10-2008-0008333 | A | 1/2008 | | | |
| KR | 20080008333 | A | * | 1/2008 | ............ | C07C 37/52 |
| KR | 10-2012-0102120 | A | 9/2012 | | | |
| KR | 10-2015-0028359 | A | 3/2015 | | | |
| KR | 20150028359 | A | * | 3/2015 | ............ | C07C 37/84 |
| KR | 10-2015-0096791 | A | 8/2015 | | | |
| KR | 10-1565917 | B1 | 11/2015 | | | |
| KR | 10-2016-0067877 | A | 6/2016 | | | |
| KR | 10-1734099 | B1 | 5/2017 | | | |
| KR | 10-2019-0124889 | A | 11/2019 | | | |
| KR | 10-2020-0014004 | A | 2/2020 | | | |
| KR | 10-2090680 | B1 | 3/2020 | | | |
| TW | 201518256 | A | 5/2015 | | | |
| WO | 2006114893 | A1 | 11/2006 | | | |
| WO | 2014-099550 | A1 | 6/2014 | | | |
| WO | 2020-257237 | A1 | 12/2020 | | | |
| WO | 2020257234 | A1 | 12/2020 | | | |
| WO | 2022113847 | A1 | 6/2022 | | | |
| WO | 2023200247 | A1 | 10/2023 | | | |

* cited by examiner

MONOMER COMPOSITION FOR SYNTHESIZING RECYCLED PLASTIC, PREPARATION METHOD THEREOF, RECYCLED PLASTIC, AND MOLDED PRODUCT USING THE SAME

CROSS-REFERENCE TO RELATED APPLICATION(S)

This application is a National Phase entry pursuant to 35 U.S.C. § 371 of International Application No. PCT/KR2022/010315, filed on Jul. 14, 2022, and claims priority to and the benefit of Korean Patent Application No. 10-2021-0122001, filed on Sep. 13, 2021, Korean Patent Application No. 10-2021-0122002, filed on Sep. 13, 2021, Korean Patent Application No. 10-2021-0122003, filed on Sep. 13, 2021, Korean Patent Application No. 10-2021-0122004, filed on Sep. 13, 2021, Korean Patent Application No. 10-2021-0128892, filed on Sep. 29, 2021, and Korean Patent Application No. 10-2021-0136153, filed on Oct. 13, 2021 in the Korean Intellectual Property Office, the entire contents of which are incorporated herein by reference.

TECHNICAL FIELD

The present disclosure relates to a monomer composition for synthesizing recycled plastic that contains a high-purity aromatic diol compound recovered through recycling by chemical decomposition of a polycarbonate-based resin, a method for preparing the same, and a recycled plastic and molded product using the same.

Also, the present disclosure relates to a monomer composition for synthesizing recycled plastic that contains a by-product with a high added value recovered through recycling by chemical decomposition of a polycarbonate-based resin, a method for preparing the same, and a recycled plastic and molded product using the same.

BACKGROUND

Polycarbonate is a thermoplastic polymer and is a plastic having excellent characteristics such as excellent transparency, ductility, and relatively low manufacturing cost.

Although polycarbonate is widely used for various purposes, environmental and health concerns during waste treatment have been continuously raised.

Currently, a physical recycling method is carried out, but in this case, a problem accompanying the deterioration of the quality occurs, and thus, research on the chemical recycling of polycarbonate is underway.

Chemical decomposition of polycarbonate refers to obtaining an aromatic diol compound as a monomer (e.g., bisphenol A (BPA)) through decomposition of polycarbonate, and then utilizing it again in polymerization to obtain a high-purity polycarbonate.

For such a chemical decomposition, thermal decomposition, hydrolysis, and alcohol decomposition are typically known. Among these, the most common method is alcohol decomposition using a base catalyst, but in the case of methanol decomposition, there is a problem that methanol is used which is harmful to the human body, and in the case of ethanol, there is a problem that high temperature and high pressure conditions are required and the yield is not high.

In addition, although an alcohol decomposition method using an organic catalyst is known, it is disadvantageous in terms of economics.

The background description provided herein is for the purpose of generally presenting context of the disclosure. Unless otherwise indicated herein, the materials described in this section are not prior art to the claims in this application and are not admitted to be prior art, or suggestions of the prior art, by inclusion in this section.

DETAILED DESCRIPTION

Technical Problem

It is an object of the present disclosure to provide a monomer composition for synthesizing recycled plastic that can secure a high-purity aromatic diol compound recovered through recycling by chemical decomposition of a polycarbonate-based resin.

It is another object of the present disclosure to provide a method for preparing the monomer composition for synthesizing recycled plastic, and a recycled plastic, and molded product using the monomer composition for synthesizing recycled plastic.

Technical Solution

In order to achieve the above object, provided herein is a monomer composition for synthesizing recycled plastic, comprising: an aromatic diol compound, wherein an impurity ratio according to the following Equation 1 is 1.2% or less, wherein the aromatic diol compound yield according to the following Equation 2 is more than 65%, and wherein the monomer composition is a recovered product from a polycarbonate-based resin:

$$\text{Impurity ratio} = \{(\text{Total peak area on liquid chromatography} - \text{Bisphenol A peak area on liquid chromatography})/\text{Total peak area on liquid chromatography}\} \times 100, \quad \text{[Equation 1]}$$

$$\text{Yield } (\%) = W_1/W_0 \quad \text{[Equation 2]}$$

wherein in Equation 2, $W_0$ is a mass of the aromatic diol compound obtained during 100% decomposition of the polycarbonate-based resin, and $W_1$ is a mass of the aromatic diol compound actually obtained.

Also provided herein is a method for preparing a monomer composition for synthesizing recycled plastic, the method comprising the steps of: depolymerizing a polycarbonate-based resin; adding a first base to adjust the pH of the depolymerization reaction product to be 12 or more; adding water after the addition of the first base to separate a carbonate precursor from the depolymerization reaction product; and adding an acid to adjust the pH of the depolymerization reaction product from which the carbonate precursor has been separated to be 4 or less.

Further provided herein is a recycled plastic comprising a reaction product of the monomer composition and a comonomer.

Further provided herein is a molded product comprising the recycled plastic.

Below, a monomer composition for synthesizing recycled plastic, a method for preparing the same, and a recycled plastic, and molded product using the same according to specific embodiments of the present disclosure will be described in more detail.

Unless explicitly stated herein, the technical terms used herein are for the purpose of describing specific embodiments only and is not intended to limit the scope of the invention.

The singular forms "a," "an" and "the" used herein are intended to include plural forms, unless the context clearly indicates otherwise.

The 'pH' as used herein means a hydrogen ion concentration (pH), which is a numerical value indicating the acidity and alkalinity of a material. The PH can be determined from a value expressed by taking the reciprocal of the logarithmic dissociation concentration of hydrogen ions, and is used as a measure of the strength of acids and bases of a material.

It should be understood that the terms "comprise," "include", "have", etc. are used herein to specify the presence of stated feature, region, integer, step, action, element and/or component, but do not preclude the presence or addition of one or more other feature, region, integer, step, action, element, component and/or group.

Further, the terms including ordinal numbers such as "a first", "a second", etc. are used only for the purpose of distinguishing one component from another component, and are not limited by the ordinal numbers. For instance, a first component may be referred to as a second component, or similarly, the second component may be referred to as the first component, without departing from the scope of the present disclosure.

1. Monomer Composition for Synthesizing Recycled Plastic

According to one embodiment of the present disclosure, there can be provided a monomer composition for synthesizing recycled plastic, which comprises an aromatic diol compound, wherein an impurity ratio according to the following Equation 1 is 1.2% or less, wherein the aromatic diol compound yield according to the following Equation 2 is more than 65%, and wherein the monomer composition for synthesizing recycled plastic is recovered from a polycarbonate-based resin:

$$\text{Impurity ratio} = \{(\text{Total peak area on liquid chromatography} - \text{Bisphenol A peak area on liquid chromatography})/\text{Total peak area on liquid chromatography}\} \times 100, \quad \text{[Equation 1]}$$

$$\text{Yield (\%)} = W_1/W_0 \quad \text{[Equation 2]}$$

in Equation 2, $W_0$ is the mass of the aromatic diol compound obtained during 100% decomposition of polycarbonate-based resin, and $W_1$ is the mass of the aromatic diol compound actually obtained.

The present inventors have found through experiments that although the monomer composition for synthesizing recycled plastics of the one embodiment was recovered through recycling by chemical decomposition of the polycarbonate-based resin, the aromatic diol compound, which is the main recovery target, is secured in high purity and high yield, whereby excellent physical properties can be realized when synthesizing polycarbonate-based resins using the same, and completed the present disclosure.

In particular, along with the monomer composition (first composition) for synthesizing recycled plastics of the one embodiment, the monomer composition (second composition) for synthesizing recycled plastic which comprises diethyl carbonate wherein the diethyl carbonate is recovered from a polycarbonate-based resin, can be respectively simultaneously obtained in a method for preparing a monomer composition for synthesizing recycled plastics, which will be described later.

That is, the present disclosure may have technical features that a first composition comprising an aromatic diol compound is obtained with high purity through recycling by chemical decomposition of polycarbonate-based resin, and at the same time, a second composition comprising diethyl carbonate, which is a by-product with a high added value, can also be obtained.

Specifically, the monomer composition for synthesizing recycled plastics of the one embodiment is characterized by being recovered from a polycarbonate-based resin. That is, this means that recovery is performed from the polycarbonate-based resin in order to obtain the monomer composition for synthesizing recycled plastics of the one embodiment, and as a result, the monomer composition for synthesizing recycled plastics containing the aromatic diol compound is obtained together.

The polycarbonate-based resin is meant to include both a homopolymer and a copolymer containing a polycarbonate repeating unit, and collectively refers to a reaction product obtained through a polymerization reaction or a copolymerization reaction of a monomer containing an aromatic diol compound and a carbonate precursor. When it contains one carbonate repeating unit obtained by using only one aromatic diol compound and one carbonate precursor, a homopolymer can be synthesized. In addition, when one aromatic diol compound and two or more carbonate precursors are used as the monomer, or two or more aromatic diol compounds and one carbonate precursor are used, or one or more other diols is used in addition to the one aromatic diol compound and the one carbonate precursor to contain two or more carbonates, a copolymer can be synthesized. The homopolymer or copolymer can include all of low-molecular compounds, oligomers, and polymers depending on the molecular weight range.

Further, the monomer composition (first composition) for synthesizing recycled plastics of the one embodiment may include an aromatic diol compound. Specific examples of the aromatic diol compound include bis(4-hydroxyphenyl) methane, bis(4-hydroxyphenyl)ether, bis(4-hydroxyphenyl) sulfone, bis(4-hydroxyphenyl)sulfoxide, bis(4-hydroxyphenyl)sulfide, bis(4-hydroxyphenyl) ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl) propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, or a mixture of two or more thereof, and the like. Preferably, the aromatic diol compound of the monomer composition (first composition) for synthesizing recycled plastics of the one embodiment may be 2,2-bis(4-hydroxyphenyl)propane (bisphenol A).

The aromatic diol compound is characterized by being recovered from the polycarbonate-based resin used for recovering the monomer composition for synthesizing the recycled plastic. That is, this means that recovery is performed from the polycarbonate-based resin in order to obtain the monomer composition for synthesizing recycled plastics of the one embodiment, and as a result, an aromatic diol compound is also obtained together. Therefore, apart from the recovery from the polycarbonate-based resin in order to prepare the monomer composition for synthesizing recycled plastics of the one embodiment, the case where a novel aromatic diol compound is added from the outside is not included in the category of aromatic diol compound of the present disclosure.

Specifically, "recovered from the polycarbonate-based resin" means being obtained through a depolymerization reaction of the polycarbonate-based resin. The depolymerization reaction can be carried out under acidic, neutral or basic conditions, and particularly, the depolymerization reaction can proceed under basic (alkaline) conditions. Particularly, the depolymerization reaction can be preferably carried out in the presence of an ethanol solvent, as will be described later.

Meanwhile, the monomer composition for synthesizing recycled plastics of the one embodiment may have a color coordinate b* value of 0 to 4.2, or 1 to 4, or 1 to 3, or 1.5 to 2.5, or 1.5 to 2.4, or 1.57 to 2.24. Also, the monomer composition for synthesizing recycled plastics of the one embodiment may have a color coordinate L* of 94 or more, 95 or more, or 100 or less, or 94 to 100, or 94 to 98, or 95 to 100, or 95 to 98, or 95.9 to 97.1. Further, the monomer composition for synthesizing recycled plastics of the one embodiment may have a color coordinate a* of 0.5 or less, or 0.3 or less, or 0 or more, or 0.01 or more, or 0 to 0.5, or 0 to 0.3, or 0.01 to 0.5, or 0.01 to 0.3, or 0.01 to 0.25.

As used herein, the "color coordinates" means coordinates in the CIE Lab color space, which are color values defined by CIE (Commossion International de l'Eclairage), and an arbitrary position in the CIE color space may be represented by three coordinate values, i.e., L*, a*, and b*.

Here, the L* value represents brightness, when L*=0, it represents black, and when L*=100, it represents white. In addition, the a* value represents a color having a corresponding color coordinate that leans toward one of pure red and pure green, and the b* value represents a color having a corresponding color coordinate that leans toward one of pure yellow and pure blue.

Specifically, the a* value is in the range of –a to +a. A maximum value of a* (a* max) represents pure red, and a minimum value of a* (a* min) represents pure green. Further, the b* value is in the range of –b to +b. A maximum value of b* (b* max) represents pure yellow, and a minimum value of b* (b* min) represents pure blue. For example, a negative b* value represents a color leaning toward pure blue, and a positive b* value represents color leaning toward pure yellow. When comparing b*=50 with b*=80, b*=80 is closer to pure yellow than b*=50.

When the color coordinate a* value of the monomer composition for synthesizing recycled plastics of the one embodiment excessively increases to more than 0.5, or the color coordinate L* value excessively decreases to less than 94, the monomer composition for synthesizing recycled plastics of the one embodiment deteriorates in color characteristics.

Meanwhile, when the color coordinate b* value of the monomer composition for synthesizing recycled plastics of the one embodiment excessively increases to more than 4.2, the monomer composition for synthesizing recycled plastics of the one embodiment represents a color excessively leaning toward yellow, resulting in poor color characteristics.

Further, when the color coordinate b* value of the monomer composition for synthesizing recycled plastics of the one embodiment excessively decreases to less than 0, the monomer composition for synthesizing recycled plastics of the one embodiment represents a color excessively leaning toward blue, resulting in poor color characteristics.

Examples of the method for measuring the color coordinates L*, a*, b* values of the monomer composition for synthesizing recycled plastics of the one embodiment are not particularly limited, and various color characteristic measurement methods in the field of plastics can be applied without limitation.

However, the color coordinates L*, a*, and b* values of the monomer composition for synthesizing recycled plastics of the one embodiment can be measured in reflection mode using HunterLab UltraScan PRO Spectrophotometer as an example.

Meanwhile, the monomer composition for synthesizing recycled plastics of the one embodiment may have an aromatic diol compound purity of 99% or more, or 100% or less, or 99% to 100%, or 99% to 99.9%, or 99% to 99.8%, or 99% to 99.7%.

Examples of the method for measuring the purity of the aromatic diol compound of the monomer composition for synthesizing recycled plastics of the one embodiment are not particularly limited, and for example, 1H NMR, ICP-MS analysis, HPLC analysis, UPLC analysis, etc. can be used without limitation. As for the specific methods, conditions, equipment, etc. of the NMR, ICP-MS, HPLC, and UPLC, various well-known contents can be applied without limitation.

An example of a method for measuring the purity of the aromatic diol compound of the monomer composition for synthesizing recycled plastics of the one embodiment is follows. 1 wt % of the monomer composition for synthesizing recycled plastics of the one embodiment was dissolved in acetonitrile (ACN) solvent under normal pressure and 20 to 30° C. conditions, and then the purity of bisphenol A (BPA) was analyzed by ultraperformance liquid chromatography (UPLC) on a Waters HPLC system using ACQUITY UPLC®BEH C18 1.7 μm (2.1*50 mm column).

As described above, in the monomer composition for synthesizing recycled plastics of the one embodiment, the purity of the aromatic diol compound, which is the main recovery target material, is remarkably increased to 99% or more, and other impurities are minimized, thereby capable of achieving excellent physical properties when synthesizing a polycarbonate-based resin using the same.

Meanwhile, the monomer composition for synthesizing recycled plastics may further include impurities other than the aromatic diol compound. The impurity refers to all materials except for the aromatic diol compound, which is the main recovery target material of the present disclosure, and the specific type thereof is not particularly limited, but for example, it may include p-tert-butylphenol.

Further, the monomer composition for synthesizing recycled plastics may have an impurity ratio according to the Equation 1 of 1.2% or less, or 0.9% or less, or 0.8% or less, or 0.7% or less, or 0.5% or less, or 0.1% or more, or 0.1% to 1.2%, or 0.1% to 0.9%, or 0.1% to 0.8%, or 0.1% to 0.7%, or 0.1% to 0.5%.

An example of a method for measuring the impurity ratio of the monomer composition for synthesizing recycled plastics of the one embodiment is not particularly limited, and, for example, LC analysis may be used. As for the specific method, conditions, equipment, etc. of the LC, various well-known contents can be applied without limitation.

As described above, in the monomer composition for synthesizing recycled plastics of the one embodiment, the ratio of impurities other than the aromatic diol compound, which is the main recovery target material, is extremely reduced to 1.2% or less, whereby excellent physical properties can be realized when synthesizing polycarbonate-based resins using the same.

Meanwhile, the monomer composition for synthesizing recycled plastics of the one embodiment may have an aromatic diol compound yield of more than 65%, or more than 67%, or more than 68%, or 100% or less, or more than 65% and 100% or less, or 67% to 100%, or 68% to 100%. Increasing the yield of the aromatic diol compound to more than 65% is considered to be due to the method for preparing a monomer composition for synthesizing recycled plastics, which will be described later.

An example of a method for measuring the yield of the aromatic diol compound of the monomer composition for synthesizing recycled plastics of the one embodiment is not particularly limited, and for example, the yield can be calculated through the following Equation 2.

$$\text{Yield (\%)} = W_1/W_0 \qquad \text{[Equation 2]}$$

in Equation 2, $W_0$ is the mass of the aromatic diol compound obtained during 100% decomposition of polycarbonate-based resin, and $W_1$ is the mass of the aromatic diol compound actually obtained.

For the measurement of the mass of the aromatic diol compound in Equation 2, various well-known mass measurement methods can be used without limitation, and for example, a scale can be used.

As described above, in the monomer composition for synthesizing recycled plastics of the one embodiment, the yield of the aromatic diol compound, which is the main recovery target material, is extremely increased to more than 65%, thereby capable of enhancing the efficiency of the recycling process for the polycarbonate-based resin.

Meanwhile, in the monomer composition for synthesizing recycled plastics of the one embodiment, diethyl carbonate can be obtained as a by-product. The diethyl carbonate is characterized by being recovered from the polycarbonate-based resin used for recovering the monomer composition for recycling plastic synthesis of the one embodiment.

That is, this means that recovery is performed from the polycarbonate-based resin in order to obtain the monomer composition for synthesizing recycled plastics of the one embodiment, and as a result, diethyl carbonate is also obtained together. Therefore, apart from the recovery from the polycarbonate-based resin in order to prepare the monomer composition for synthesizing recycled plastics of the one embodiment, the case where a novel diethyl carbonate is added from the outside is not included in the category of diethyl carbonate of the present disclosure.

Specifically, "recovered from the polycarbonate-based resin" means being obtained through a depolymerization reaction of the polycarbonate-based resin. The depolymerization reaction can be carried out under acidic, neutral or basic conditions, and particularly, the depolymerization reaction can proceed under basic (alkaline) conditions. Particularly, the depolymerization reaction can be preferably carried out in the presence of an ethanol solvent, as will be described later.

Since the main recovery target material in the monomer composition for synthesizing recycled plastics of the one embodiment is an aromatic diol compound, the diethyl carbonate can be separately separated and recovered as the by-product from the monomer composition for synthesizing recycled plastics of the one embodiment.

The monomer composition for synthesizing recycled plastics of the one embodiment can be used as a raw material for preparing various recycled plastics (e.g., polycarbonate (PC)) which will be described later.

The monomer composition for synthesizing recycled plastics of the one embodiment may further include small amounts of other additives and solvents. Specific types of the additives or solvents are not particularly limited, and various materials widely used in the process of recovering the aromatic diol compound by a depolymerization of the polycarbonate-based resin can be applied without limitation.

The monomer composition for synthesizing recycled plastics of the one embodiment can be obtained by a method for preparing a monomer composition for synthesizing recycled plastics, which will be described later. That is, the monomer composition for synthesizing recycled plastics of one embodiment corresponds to the result obtained through various processes of filtration, purification, washing, and drying in order to secure only the aromatic diol compound, which is the main recovery target material, with high purity after the depolymerization reaction of the polycarbonate-based resin.

2. Method for Preparing a Monomer Composition for Synthesizing Recycled Plastic

According to another embodiment of the present disclosure, there can be provided a method for preparing a monomer composition for synthesizing recycled plastic, the method comprising the steps of: depolymerizing a polycarbonate-based resin; adding a base so that the pH of the depolymerization reaction product is 12 or more; adding water after the addition of base to separate a carbonate precursor from the depolymerization reaction product; and adding an acid so that the pH of the depolymerization reaction product from which the carbonate precursor has been separated is 4 or less.

The present inventors confirmed through experiments that similarly to the method for preparing the monomer composition for synthesizing recycled plastic of the other embodiments, the pH of the depolymerized polycarbonate resin is stepwisely adjusted in the process of recycling polycarbonate-based resin by chemical decomposition, whereby the aromatic diol compound, which is the main synthetic target material in the present disclosure, can be secured with high purity and high yield within a fast process time, and completed the present disclosure.

In particular, distillation has been used in the past to remove carbonate monomers from the depolymerized polycarbonate-based resin, but the present invention has an advantage that through stepwise adjustment of pH instead of distillation, the aromatic diol compound can be obtained in a high yield for a faster process time than during distillation.

Specifically, the method for preparing the monomer composition for synthesizing recycled plastics of the other embodiment may comprise a step of depolymerizing a polycarbonate-based resin.

The polycarbonate-based resin is meant to include both a homopolymer and a copolymer containing a polycarbonate repeating unit, and collectively refers to a reaction product obtained through a polymerization reaction or a copolymerization reaction of a monomer containing an aromatic diol compound and a carbonate precursor. When it contains one carbonate repeating unit obtained by using only one aromatic diol compound and one carbonate precursor, a homopolymer can be synthesized. In addition, when one aromatic diol compound and two or more carbonate precursors are used as the monomer, or two or more aromatic diol compounds and one carbonate precursor are used, or one or more other diols is used in addition to the one aromatic diol compound and the one carbonate precursor to contain two or more carbonates, a copolymer can be synthesized. The homopolymer or copolymer can include all of low-molecular compounds, oligomers, and polymers depending on the molecular weight range.

The polycarbonate-based resin can be applied regardless of various forms and types, such as a novel polycarbonate-based resin produced through synthesis, a recycled polycarbonate-based resin produced through a regeneration process, or polycarbonate-based resin waste.

However, if necessary, before proceeding the depolymerization reaction of the polycarbonate-based resin, a pretreatment step of the polycarbonate-based resin is carried out, thereby capable of increasing the efficiency of the process of recovering an aromatic diol compound and a carbonate precursor from the polycarbonate-based resin. Examples of the pretreatment process may include washing, drying, grinding, glycol decomposition, and the like. The specific method of each pretreatment process is not limited, and various methods widely used in the process of recovering the aromatic diol compound and the carbonate precursor from the polycarbonate-based resin can be applied without limitation.

During the depolymerization reaction of the polycarbonate-based resin, the depolymerization reaction can be carried out under acidic, neutral or basic conditions, and particularly, the depolymerization reaction may be carried out under basic (alkali) conditions. The type of the base is not particularly limited, and examples thereof include sodium hydroxide (NaOH) or potassium hydroxide (KOH). The base is a base catalyst acting as a catalyst, and has the economic advantages over organic catalysts, which are mainly used under mild conditions. More specifically, during the depolymerization of the polycarbonate-based resin, the depolymerization reaction can be carried out within a pH range of more than 8 and less than 12.

During the depolymerization reaction of the polycarbonate-based resin, the depolymerization reaction can be carried out by reacting a base in an amount of 0.5 mol or less, or 0.4 moles or less, or 0.3 moles or less, or 0.1 moles or more, or 0.2 mole or more, or 0.1 mole to 0.5 mole, or 0.1 mole to 0.4 mole, or 0.1 mole to 0.3 mole, or 0.2 mole to 0.5 mole, or 0.2 mole to 0.4 mole, or 0.2 mole to 0.3 mole relative to 1 mole of polycarbonate-based resin. When the polycarbonate-based resin is reacted with a base in an amount of more than 0.5 mol relative to 1 mole of the polycarbonate-based resin during depolymerization of the polycarbonate-based resin, it is limited that impurities increase due to the effect of increasing the amount of alkali salt generated, so the purity of the target recovery material is reduced, and the economic efficiency of the catalytic reaction is reduced.

Further, the depolymerization reaction of the polycarbonate-based resin can be carried out in the presence of a solvent containing ethanol. The present disclosure can stably obtain bisphenol A, which is a high-purity monomer, by decomposing a polycarbonate-based resin with a solvent containing ethanol, and has the advantage that diethyl carbonate having a high added value can be further obtained as a reaction by-product.

The content of the ethanol may be 5 to 15 moles, or 8 to 13 moles relative to 1 mole of the polycarbonate-based resin. Since the ethanol has good solubility in bisphenol A, ethanol within the above range should be essentially contained. When the content of the ethanol is excessively reduced to less than 5 moles relative to 1 mole of the polycarbonate-based resin, it is difficult to sufficiently progress the alcohol decomposition of polycarbonate-based resin. On the other hand, when the content of ethanol is excessively increased to more than 15 moles relative to 1 mole of the polycarbonate-based resin, the economics of the process can be reduced due to excessive use of alcohol.

The solvent in which the depolymerization reaction of the polycarbonate-based resin proceeds may further include, in addition to ethanol, at least one organic solvent selected from the group consisting of tetrahydrofuran, toluene, methylene chloride, chloroform, dimethyl carbonate, ethylmethyl carbonate, diethyl carbonate, and dipropyl carbonate.

The organic solvent may include tetrahydrofuran, toluene, methylene chloride, chloroform, dimethyl carbonate, ethylmethyl carbonate, diethyl carbonate, dipropyl carbonate, or a mixture of two or more thereof.

More preferably, methylene chloride can be used as the organic solvent. When methylene chloride is used as an organic solvent to be mixed with the ethanol, there is an advantage that the dissolution properties in polycarbonate can be improved and the reactivity can be improved.

The content of the organic solvent may be 16 moles to 20 moles, or 16 moles to 18 moles relative to 1 mole of the polycarbonate-based resin. In addition, the content of the organic solvent may be 1.5 moles to 2 moles relative to 1 mole of ethanol. By mixing the polycarbonate-based resin, ethanol, and an organic solvent within the above range, there is an advantage that the depolymerization reaction of the polymer can proceed at a desired level.

Meanwhile, the temperature at which the depolymerization reaction of the polycarbonate-based resin proceeds is not particularly limited, but for example, the reaction may proceed at a temperature of 20° C. to 100° C., or 50° C. to 70° C. In addition, the depolymerization of the polycarbonate-based resin may proceed for 1 hour to 30 hours, or 4 hours to 6 hours.

Specifically, the conditions are mild process conditions relative to the conventional pressurizing/high temperature process, and by performing stirring under the above conditions, the process can be performed in a mild process as compared to the pressurizing/high temperature process. In particular, when stirring at 50° C. to 70° C. for 4 to 6 hours, there is an advantage of obtaining the most efficient results in terms of reproducibility and acceptability.

That is, according to the present disclosure, by adjusting the type and mixing amount of the mixed solvent and the type and content of the base catalyst without using an organic catalyst, there is the advantage that a high-purity aromatic diol compound (e.g., bisphenol A) can be obtained under mild conditions without using a pressure/high temperature process, and diethyl carbonate can be obtained as a by-product by using an ethanol solvent.

More specifically, the step of depolymerizing the polycarbonate-based resin may include a first step of dissolving the carbonate-based resin in an organic solvent; and a second step of adding and stirring a catalyst solution containing ethanol and a base. In the first and second steps, the contents of ethanol, organic solvent, base, and polycarbonate-based resin are the same as described above.

Meanwhile, the method for preparing the monomer composition for synthesizing recycled plastics of the other embodiment may further include a step of adding a base so that the pH of the depolymerization reaction product is 12 or more, or 12 to 14. The base may be a strong base, and examples thereof include sodium hydroxide (NaOH).

In the step of adding a base so that the pH of the depolymerization reaction product is 12 or more, the aromatic diol compound contained in the depolymerization reaction product may be converted into a salt of the aromatic diol compound.

In the step of adding water after the addition of base to separate a carbonate precursor from the depolymerization reaction product, the depolymerization reaction product may form a layer divided into a water layer containing the salt of the aromatic diol compound and an organic solvent layer containing diethyl carbonate. Since the salt of the aromatic diol compound has hydrophilicity, it may be contained in the water layer among water and organic solvents, and since diethyl carbonate has hydrophobicity, it may be contained in the organic solvent layer among water and organic solvents. Thereby, an aromatic diol compound as a main product and diethyl carbonate as a by-product can be easily separated only by a simple process of changing the pH.

Meanwhile, the method for preparing a monomer composition for synthesizing recycled plastic of the other embodiment may include a step of adding water after the addition of base to separate a carbonate precursor from the depolymerization reaction product. Therefore, the separated carbonate precursor may include diethyl carbonate.

As described above, as a step of adding water after the addition of base to separate a carbonate precursor from the depolymerization reaction product proceeds after the step of adding a base so that the pH of the depolymerization reaction product is 12 or more, the depolymerization reaction product forms a layer divided into a water layer containing a salt of an aromatic diol compound, and an organic solvent layer containing diethyl carbonate, whereby a layer divided by an organic solvent layer containing diethyl carbonate can be separated.

In the step of adding water after the addition of base to separate a carbonate precursor from the depolymerization reaction product, the organic layer is separated from the water layer so that the carbonate precursor can be recovered from the separated organic layer. Specific separation conditions for separating the organic layer from the water layer are not particularly limited, and as for the specific separation devices and methods, various well-known purification techniques can be applied without limitation. However, in one example, a separatory funnel can be used.

The separated carbonate precursor can be recycled without a separate separation and purification process, or can be recycled through separation and purification such as conventional extraction, adsorption, and drying, if necessary. Specific purification conditions are not particularly limited. As for the specific purification devices and methods, various well-known purification techniques can be applied without limitation.

Meanwhile, the method may include a step of adding an acid so that the pH of the depolymerization reaction product from which the carbonate precursor has been separated is 4 or less, or 2 or less, or 1 to 4, or 1 to 2. Thereby, an aromatic diol compound, which is a main recovery material, is obtained, which corresponds to the monomer composition for synthesizing recycled plastic according to the one embodiment.

As described above, as the step of adding water after the addition of base to separate a carbonate precursor from the depolymerization reaction product proceeds after the step of adding a base so that the pH of the depolymerization reaction product is 12 or more, the depolymerization reaction product may form a layer divided into a water layer containing a salt of an aromatic diol compound, and an organic solvent layer containing diethyl carbonate. And, as the organic layer is separated from the water layer, a water layer containing a salt of an aromatic diol compound remains in the depolymerization reaction product after the step of separating the carbonate precursor from the depolymerization reaction product.

Since the main recovery target material of the present disclosure is an aromatic diol compound, the salt of the aromatic diol compound contained in the water layer can be converted into an aromatic diol compound through an additional acid neutralization step. That is, in the step of adding an acid so that the pH of the depolymerization reaction product from which the carbonate precursor has been separated is 4 or less, the salt of the aromatic diol compound contained in the depolymerization reaction product can be converted into the aromatic diol compound.

The acid may be a strong acid, and examples thereof include hydrochloric acid (HCl).

Meanwhile, the method for preparing the monomer composition for synthesizing recycled plastics of the other embodiment may further include a step of purifying the depolymerization product from which the carbonate precursor has been separated, after the step of adding an acid so that the pH of the depolymerization reaction product from which the carbonate precursor has been separated is 4 or less.

Specifically, the purification step of the depolymerization reaction product from which the carbonate precursor has been separated may include a step of washing the depolymerization reaction product from which the carbonate precursor has been separated. Also, the purification step of the depolymerization reaction product from which the carbonate precursor has been separated may include an adsorption purification step of the depolymerization reaction product from which the carbonate precursor has been separated. Further, the purification step of the depolymerization reaction product from which the carbonate precursor has been separated may include a recrystallization step of the depolymerization reaction product from which the carbonate precursor has been separated.

The order of the washing step; the adsorption purification step; or the recrystallization step is not particularly limited, and it is irrelevant to proceed in any order, but for example, the washing step; the adsorption purification step; and the recrystallization step can proceed in this order. The washing step; the adsorption purification step; and the recrystallization step can proceed repeatedly at least once or more, respectively. As for the specific washing, adsorption, and recrystallization devices and methods, various well-known purification techniques can be applied without limitation.

Specifically, in the washing step of the depolymerization reaction product from which the carbonate precursor has been separated, the depolymerization reaction product from which the carbonate precursor has been separated may contain an aromatic diol compound. However, since various impurities remain during the recovery process of obtaining the aromatic diol compound, washing can proceed in order to sufficiently remove these impurities and secure a high-purity aromatic diol compound.

Specifically, the washing step may include a step of washing with a solvent at a temperature of 10° C. or more and 30° C. or less, or 20° C. or more and 30° C. or less; and a step of washing with a solvent at a temperature of 40° C. or more and 80° C. or less, or 40° C. or more and 60° C. or less, or 45° C. or more and 55° C. or less. The temperature condition means the temperature inside the washing container at which washing with a solvent is performed. In order to maintain a high temperature deviating from a room temperature, various heating devices can be applied without limitation.

In the washing step, the step of washing with a solvent at a temperature of 10° C. or more and 30° C. or less may be performed first, and the step of washing with a solvent at a temperature of 40° C. or more and 80° C. or less may be performed later. Alternatively, the step of washing with a solvent at a temperature of 40° C. or more and 80° C. or less may be performed first, and the step of washing with a solvent at a temperature of 10° C. or more and 30° C. or less may be performed later.

More preferably, in the washing step, the step of washing with a solvent at a temperature of 10° C. or more and 30° C. or less may be performed first, and the step of washing with a solvent at a temperature of 40° C. or more and 80° C. or less may be performed later. Thereby, the corrosion of the reactor due to strong acid after the neutralization step can be minimized.

The step of washing with a solvent at a temperature of 10° C. or more and 30° C. or less; and the step of washing with a solvent at a temperature of 40° C. or more and 80° C. or less can be repeated at least once or more, respectively.

Further, if necessary, after proceeding the step of washing with a solvent at a temperature of 10° C. or more and 30° C. or less; and the step of washing with a solvent at a temperature of 40° C. or more and 80° C. or less, a step of removing the residual solvent through filtration may be further performed.

More specifically, the difference value between the temperature of the step of washing with a solvent at a temperature of 40° C. or more and 80° C. or less and the temperature of the step of washing with a solvent at a temperature of 10° C. or more and 30° C. or less may be 20° C. or more and 50° C. or less.

The difference value between the temperature of the step of washing with a solvent at a temperature of 40° C. or more and 80° C. or less and the temperature of the step of washing with a solvent at a temperature of 10° C. or more and 30° C. or less means a value obtained by subtracting the temperature of the step of washing with a solvent at a temperature of 10° C. or more and 30° C. or less from the temperature of the step of washing with a solvent at a temperature of 40° C. or more and 80° C. or less.

When the difference value between the temperature of the step of washing with a solvent at a temperature of 40° C. or more and 80° C. or less and the temperature of the step of washing with a solvent at a temperature of 10° C. or more and 30° C. or less decreases excessively to less than 20° C., it is difficult to sufficiently remove impurities.

When the difference value between the temperature of the step of washing with a solvent at a temperature of 40° C. or more and 80° C. or less and the temperature of the step of washing with a solvent at a temperature of 10° C. or more and 30° C. or less increases excessively to more than 50° C., severe conditions are formed to maintain extreme temperature conditions, which can reduce the efficiency of the process.

The solvent used in the washing step may include one of water, alcohol, and an organic solvent. As the organic solvent, tetrahydrofuran, toluene, methylene chloride, chloroform, dimethyl carbonate, ethylmethyl carbonate, diethyl carbonate, dipropyl carbonate, or a mixture of two or more thereof can be used.

The solvent used in the washing step can be used in a weight ratio of 1 part by weight or more and 30 parts by weight or less, or 1 part by weight or more and 10 parts by weight or less based on 1 part by weight of the polycarbonate-based resin used in the depolymerization reaction.

More specifically, the solvent in the step of washing with a solvent at a temperature of 10° C. or more and 30° C. or less may be an organic solvent. Preferably, methylene chloride can be used as the organic solvent. At this time, the organic solvent can be used in an amount of 1 part by weight or more and 10 parts by weight or less based on 1 part by weight of the polycarbonate-based resin.

Moreover, the solvent in the step of washing with a solvent at a temperature of 40° C. or more and 80° C. or less may be water. When water is used, impurities in the form of residual salts can be effectively removed. At this time, the solvent can be used in an amount of 1 part by weight or more and 10 parts by weight or less based on 1 part by weight of the polycarbonate-based resin.

Further, the adsorption purification step of the depolymerization reaction product from which the carbonate precursor has been separated may include a step of adding an adsorbent to the depolymerization reaction product from which the carbonate precursor has been separated to perform an absorption purification and then removing the adsorbent. In the step of adding an adsorbent to the depolymerization reaction product from which the carbonate precursor has been separated to perform an absorption purification and then removing the adsorbent, an adsorbent can be brought into contact with the depolymerization reaction product.

Examples of the adsorbent that can be used include activated carbon, charcoal, or a mixture thereof. The activated carbon is a black carbon material having micropores produced by subjecting a raw material to a carbonization process at about 500° C. and an activated carbon process at about 900° C., and examples thereof are not particularly limited, but for example, various activated carbons such as plant-based, coal-based, petroleum-based, waste-based activated carbons can be applied without limitation depending on the type of raw material.

In more specific examples, the plant-based activated carbon may include coconut activated carbon, wood activated carbon, and sawdust activated carbon. Further, the coal-based activated carbon may include lignite activated carbon, bituminous coal activated carbon, and anthracite activated carbon. Further, the petroleum-based activated carbon may include petroleum coke activated carbon and oil carbon activated carbon. Further, the waste activated carbon may include synthetic resin activated carbon and pulp activated carbon.

The adsorbent may include at least one activated carbon selected from the group consisting of plant-based activated carbon, coal-based activated carbon, petroleum-based activated carbon, and waste-based activated carbon. That is, the adsorbent may include plant-based activated carbon, coal-based activated carbon, petroleum-based activated carbon, waste-based activated carbon, or a mixture of two or more thereof.

More specifically, the adsorbent may include at least one activated carbon selected from the group consisting of coconut activated carbon, lignite activated carbon, anthracite activated carbon, and bituminous coal activated carbon. That is, the first adsorbent may include coconut activated carbon, lignite activated carbon, anthracite activated carbon, bituminous coal activated carbon, or a mixture of two or more thereof.

Adsorption purification conditions by the adsorbent are not particularly limited, and various well-known adsorption purification conditions can be used without limitation. However, in one example, the addition amount of the adsorbent may be 40% to 60% by weight relative to the polycarbonate-based resin, and the adsorption time may be 1 hour to 5 hours, and the adsorption method may be a stirring adsorption or an adsorption tower for Lab.

If necessary, the method may further include a step of adding a solvent to the depolymerization reaction product from which the carbonate precursor has been separated, prior to the step of adding an adsorbent to the depolymerization reaction product from which the carbonate precursor has been separated to perform an adsorption purification and then removing the adsorbent. Examples of the solvent include ethanol, and the ethanol may be added in a ratio of 1 mole to 20 moles, or 10 moles to 20 moles, or 15 moles to 20 moles relative to 1 mole of the polycarbonate-based resin. Aromatic diol compound crystals included in the depolymerization reaction product from which the carbonate precursor has been separated can be redissolved in a solvent through the step of adding a solvent to the depolymerization reaction product in which the carbonate precursor has been separated.

Meanwhile, in the recrystallization step of the depolymerization reaction product from which the carbonate precursor has been separated, a high-purity aromatic diol compound can be secured by sufficiently removing various impurities contained in the depolymerization product from which the carbonate precursor has been separated.

Specifically, the recrystallization step may include a step of adding water to the depolymerization reaction product from which the carbonate precursor has been separated to perform recrystallization. Through the step of adding water to the depolymerization reaction product from which the carbonate precursor has been separated to perform recrystallization, the solubility of the aromatic diol compound or its salt contained in the depolymerization reaction product is increased, and thus, crystals, or impurities interposed between crystals can be dissolved with a solvent to the maximum, and further, since the dissolved aromatic diol compound has poor solubility relative to impurities, it can be easily precipitated into aromatic diol compound crystals through the difference in solubility when the temperature is lowered subsequently.

More specifically, in the step of adding water to the depolymerization reaction product from which the carbonate precursor has been separated to perform recrystallization, 200 moles to 400 moles, or 250 moles to 350 moles of water can be used with respect to 1 mole of the polycarbonate-based resin. When the water is used in an excessively small amount, the temperature for dissolving the aromatic diol compound contained in the depolymerization reaction product from which the carbonate precursor has been separated becomes too high, which thus deteriorates in the process efficiency, and it is difficult to remove impurities through recrystallization. On the other hand, when water is used in an excessively large amount, the solubility of the aromatic diol compound contained in the depolymerization reaction product from which the carbonate precursor has been separated becomes too high, and thus, the yield of the aromatic diol compound recovered after recrystallization is reduced, and the process efficiency can be reduced due to the use of large amounts of solvent.

If necessary, after proceeding the recrystallization step of the depolymerization reaction product from which the carbonate precursor has been separated, a step of removing residual impurities through filtration or adsorption can be further performed. In addition, if necessary, after the recrystallization step, the method may further include a drying step. The remaining solvent can be removed by the drying, and the specific drying conditions are not particularly limited, but for example, the drying can be performed at a temperature of 10° C. to 100° C., or 10° C. to 50° C. As for the specific drying equipment and method used in the drying, various well-known drying techniques can be applied without limitation.

3. Recycled Plastic

According to another embodiment of the present disclosure, a recycled plastic comprising a reaction product of the monomer composition for synthesizing recycled plastic of the one embodiment and a comonomer can be provided.

The details of the monomer composition for synthesizing recycled plastic of the one embodiment include all the contents described above in the one embodiment and the other embodiment.

Examples corresponding to the recycled plastic are not particularly limited, and various plastics synthesized from aromatic diol compounds such as bisphenol A and a carbonate precursor such as dimethyl carbonate, diethyl carbonate, or ethylmethyl carbonate as a monomer can be applied without limitation, and a more specific example may be a polycarbonate-based resin.

The polycarbonate-based resin is meant to include both a homopolymer and a copolymer containing a polycarbonate repeating unit, and collectively refers to a reaction product obtained through a polymerization reaction or a copolymerization reaction of a monomer containing an aromatic diol compound and a carbonate precursor. When it contains one carbonate repeating unit obtained by using only one aromatic diol compound and one carbonate precursor, a homopolymer can be synthesized. In addition, when one aromatic diol compound and two or more carbonate precursors are used as the monomer, or two or more aromatic diol compounds and one carbonate precursor are used, or one or more other diols is used in addition to the one aromatic diol compound and the one carbonate precursor to contain two or more carbonates, a copolymer can be synthesized. The homopolymer or copolymer can include all of low-molecular compounds, oligomers, and polymers depending on the molecular weight range.

More specifically, in the recycled plastic containing the reaction product of the monomer composition for synthesizing the recycled plastic and the comonomer of the one embodiment, a carbonate precursor can be used as the comonomer. Specific examples of the carbonate precursor include phosgene, triphosgene, diphosgene, bromophosgene, dimethyl carbonate, diethyl carbonate, dibutyl carbonate, dicyclohexyl carbonate, diphenyl carbonate, ditolyl carbonate, bis(chlorophenyl)carbonate, m-cresyl carbonate, dinaphthyl carbonate, bis(diphenyl) carbonate or bishaloformate.

Examples of the reaction process of the monomer composition for synthesizing recycled plastic and the comonomer that synthesizes the polycarbonate-based resin are not particularly limited, and various well-known methods for preparing polycarbonate can be applied without limitation.

However, in one example of the polycarbonate preparation method, a polycarbonate preparation method including the step of polymerizing a composition containing a monomer composition for synthesizing recycled plastic and a comonomer can be used. At this time, the polymerization can be carried out by interfacial polymerization, and during interfacial polymerization, polymerization reaction is possible at normal pressure and low temperature, and the molecular weight is easy to control.

The polymerization temperature may be 0° C. to 40° C., and the reaction time may be 10 minutes to 5 hours. In addition, the pH during the reaction may be maintained at 9 or more or 11 or more.

The solvent that can be used for the polymerization is not particularly limited as long as it is a solvent used for polymerization of polycarbonate in the art, and as an example, halogenated hydrocarbons such as methylene chloride and chlorobenzene can be used.

Moreover, the polymerization can be carried out in the presence of an acid binder. As the acid binder, an alkali metal hydroxide such as sodium hydroxide or potassium hydroxide, or an amine compound such as pyridine can be used.

Further, in order to control the molecular weight of the polycarbonate during the polymerization, polymerization can be performed in the presence of a molecular weight modifier. An alkylphenol having 1 to 20 carbon atoms may be used as the molecular weight modifier, and specific examples thereof include p-tert-butylphenol, p-cumylphenol, decylphenol, dodecylphenol, tetradecylphenol, hexadecylphenol, octadecylphenol, eicosylphenol, docosylphenol or triacontylphenol. The molecular weight modifier can be added before, during or after the initiation of polymerization. The molecular weight modifier may be used in an amount of 0.01 to 10 parts by weight, or 0.1 to 6 parts by weight, based on 100 parts by weight of the aromatic diol compound, and a desired molecular weight can be obtained within this range.

In addition, in order to promote the polymerization reaction, a reaction accelerator such as a tertiary amine compound, a quaternary ammonium compound, or a quaternary phosphonium compound, including triethylamine, tetra-n-butylammonium bromide, or tetra-n-butylphosphonium bromide can be further used.

4. Molded Product

According to another embodiment of the present disclosure, a molded article comprising the recycled plastic of the other embodiment can be provided. The details of the recycled plastic includes all the contents described above in the other embodiments.

The molded article can be obtained by applying the recycled plastic to various known plastic molding methods without limitation. As an example of the molding method, injection molding, foam injection molding, blow molding, or extrusion molding may be mentioned.

Examples of the molded article are not particularly limited, and can be applied to various molded articles using plastic without limitation. Examples of the molded article include automobiles, electrical and electronic products, communication products, daily necessities, building materials, optical components, exterior materials, and the like.

The molded article may further include one or more additives selected from the group consisting of an antioxidant, a plasticizer, an antistatic agent, a nucleating agent, a flame retardant, a lubricant, an impact enhancer, an optical brightener, an ultraviolet absorber, a pigment and a dye, if necessary, in addition to the recycled plastic of the other embodiments, An example of the manufacturing method of the molded article may include a step of mixing the recycled plastic of the other embodiment and an additive well using a mixer, extrusion-molding the mixture with an extruder to produce pellets, drying the pellets, and then injecting them with an injection molding machine.

Advantageous Effects

According to the present disclosure, a monomer composition for synthesizing recycled plastic that contains a high-purity and high-yield aromatic diol compound recovered through recycling by chemical decomposition of a polycarbonate-based resin, a method for preparing the same, and a recycled plastic and molded product using the same can be provided.

DETAILED DESCRIPTION OF THE EMBODIMENTS

Hereinafter, the present disclosure will be explained in detail with reference to the following examples. However, these examples are for illustrative purposes only, and the scope of the present disclosure is not limited thereto.

Example and Comparative Example: Preparation of Recycled Bisphenol A Monomer Composition Example 1

(1. Decomposition step) 1 mol of Pretreated waste polycarbonate (PC) was dissolved in 17 mol of methylene chloride (MC), and then added together with 11 mol of ethanol (EtOH) and 0.25 mol of sodium hydroxide (NaOH) to a 3L high-pressure reactor, and the mixture was stirred at 60° C. for 6 hours to proceed a PC depolymerization reaction.

(2. Basifying step) The product of the depolymerization reaction was cooled to 30° C. or less, and then the product containing bisphenol A was basified with 2 mol of 40% sodium hydroxide (NaOH) until it reached a pH of 14.

(3. Layer separation step) After that, water was further added to form a water layer and a methylene chloride (MC) layer. The methylene chloride (MC) layer located on the lower side was removed using a separatory funnel, and the water layer located on the upper side was recovered.

(4. Acidifying step) The recovered water layer was acidified by adding 10% HCl and water until it reached a pH of 1 to 2. Then, bisphenol A was recovered by filtration through vacuum filtration.

(5-1. Additional purification step—Redissolution step) Bisphenol A was added to 16.6 mol of ethanol and redissolved.

(5-2. Additional purification step—Adsorption step) After that, lignite activated carbon as the adsorbent was added at a ratio of 50 wt. % relative to waste polycarbonate, purified through adsorption for 3 hours, and filtered to remove the lignite activated carbon.

(5-3. Additional purification step—Recrystallization step) 300 mol of water was added to recrystallize bisphenol A, and then the obtained slurry was vacuum filtered at 20~30° C. to recover bisphenol A (BPA) crystals.

(6. Drying step) After that, it was vacuum dried in a convection oven at 40° C. to prepare a recycled bisphenol A monomer composition in which recycled bisphenol A (BPA) was recovered.

Example 2

A recycled bisphenol A monomer composition was prepared in the same manner as in Example 1, except that the following (Washing step) was added between (4. Acidifying step) and (5-1. Additional purification step—Redissolution step) of Example 1.

(Washing step) Primary washing was performed using methylene chloride (MC) of once the mass of used PC at 20~30° C., followed by vacuum filtration. The filtrate was secondarily washed using water of three times the mass of PC used at a temperature of 50° C.

Example 3

A recycled bisphenol A monomer composition was prepared in the same manner as in Example 1, except that (5-2. Additional purification step—Adsorption step) of Example 1 was not performed.

Comparative Example 1

A recycled bisphenol A monomer composition was prepared in the same manner as in Example 1, except that the following (Distillation step) was performed instead of (3. Layer separation step) and (4. Acidifying step) of Example 1.

(Distillation step) After that, the product lowered to pH 2 was subjected to a low-temperature distillation reducing pressure from 250 mbar and 20~30° C. to 30 mbar and 30° C.

Experimental Example

The physical properties of the recycled bisphenol A monomer compositions or by-products obtained in the Examples and Comparative Examples were measured by the following methods, and the results are shown in Table 1 below.

1. Purity 1 wt % of the recycled bisphenol A monomer composition was dissolved in acetonitrile (ACN) solvent under normal pressure and 20 to 30° C. conditions, and then the purity of bisphenol A (BPA) was analyzed by ultraperformance liquid chromatography (UPLC) on a Waters HPLC system using ACQUITY UPLC®BEH C18 1.7 μm (2.1*50 mm column).

2. Color Coordinates (L*, a*, and b*)

The color coordinates of the recycled bisphenol A monomer compositions were analyzed in reflection mode using HunterLab UltraScan PRO Spectrophotometer.

3. Yield

The weight of BPA produced when the polycarbonate used in the reaction was 100% decomposed was measured, and the weight of the obtained BPA was measured, and the yield of BPA was calculated according to the following Equation 2.

$$\text{Yield } (\%) = W_1/W_0 \qquad \text{[Equation 2]}$$

in Equation 2, $W_0$ is the mass of the aromatic diol compound obtained during 100% decomposition, and $W_1$ is the mass of the aromatic diol compound actually obtained. Specifically, when about 100 g of polycarbonate was decomposed, the mass of BPA obtained during 100% decomposition in theory is 89 g. If the mass of the actually obtained BPA is 80 g, the yield is 80/89*100=90%.

4. Impurity Ratio 1 ml of the recycled bisphenol A monomer composition was collected as a sample, subjected to ion chromatography (IC) analysis under the following conditions, and the impurity ratio was determined according to the following Equation 1. As a result of measurement using liquid chromatography, all materials except bisphenol A were regarded as impurities.

<Liquid Chromatography (LC) Conditions>

①  Column: HP-1(L:30 m, ID:0.32 mm, film:1.05 m)
②  Injection volume: 1 μℓ
③  Inlet
Temp.: 260° C., Pressure: 6.92 psi, Total flow: 64.2 ml/min,
Split flow: 60 ml/min, spilt ratio: 50:1
④  Column flow: 1.2 ml/min
⑤  Oven temp.: 70° C./3 min-10° C./min-280° C./41 min (Total 65 min)
⑥  Detector
Temp.:280° C., H₂: 35 ml/min, Air: 300 ml/min, He: 20 ml/min
⑦  GC Model: Agilent 7890

Impurity ratio={(Total peak area on liquid chromatography–Bisphenol A peak area on liquid chromatography)/Total peak area on liquid chromatography}×100,   [Equation 1]

TABLE 1

| | Measurement result of Experimental Example 1 | | | | | |
| Category | Purity (%) | L* | a* | b* | Yield (%) | Impurity (%) |
| --- | --- | --- | --- | --- | --- | --- |
| Example 1 | 99.3 | 96.4 | 0.12 | 1.82 | 72 | 0.7 |
| Example 2 | 99.7 | 97.1 | 0.01 | 1.57 | 68 | 0.3 |
| Example 3 | 99.1 | 95.9 | 0.25 | 2.24 | 73 | 0.9 |
| Comparative Example 1 | 99.1 | 96.0 | 0.34 | 2.49 | 65 | 0.9 |

As shown in Table 1, the recycled bisphenol A monomer compositions obtained in Examples 1 to 3 exhibited high purity of 99.1% to 99.7%. Also, the recycled bisphenol A monomer compositions obtained in Examples 1 to 3 exhibited a color coordinates L* of 95.9 to 97.1, a* of 0.01 to 0.25, and b* of 1.57 to 2.24, showing excellent optical properties. In addition, the recycled bisphenol A monomer compositions obtained in Examples 1 to 3 were measured to have a high BPA yield of 68% to 73%. Further, the recycled bisphenol A monomer compositions obtained in Examples 1 to 3 were measured to have a low impurity ratio of 0.3% to 0.9%. On the other hand, the recycled bisphenol A monomer composition obtained in Comparative Example 1 exhibited a color coordinate L* of 96.0, a* of 0.34, and b* of 2.49, showing poor optical properties as compared to those of Examples. In addition, the recycled bisphenol A monomer compositions obtained in Comparative Example 1 was measured to have a BPA yield of 65%, which was lower than in Examples.

The invention claimed is:

1. A monomer composition for synthesizing recycled plastic, comprising:
an aromatic diol compound,
wherein an impurity ratio according to the following Equation 1 is 1.2% or less,
wherein the aromatic diol compound yield according to the following Equation 2 is more than 65%,
wherein the monomer composition for synthesizing recycled plastic has a color coordinate L* of 96.4 or more, a color coordinate a* of 0.12 or less and a color coordinate b* of 0 to 1.82, and
wherein the monomer composition is a recovered product from a polycarbonate-based resin:

Impurity ratio={(Total peak area on liquid chromatography–Bisphenol A peak area on liquid chromatography)/Total peak area on liquid chromatography}×100,   [Equation 1]

$$\text{Yield } (\%) = W_1/W_0 \qquad \text{[Equation 2]}$$

wherein, in Equation 2, $W_0$ is a mass of the aromatic diol compound obtained during 100% decomposition of the polycarbonate-based resin, and $W_1$ is a mass of the aromatic diol compound actually obtained.

2. The monomer composition according to claim 1, wherein the monomer composition has an aromatic diol compound purity of 99% or more.

3. The monomer composition according to claim 1, further comprising:
diethyl carbonate as a by-product.

4. A method for preparing a monomer composition for synthesizing recycled plastic, the method comprising the steps of:
depolymerizing a polycarbonate-based resin;
adding a first base to adjust the pH of a depolymerization reaction product to be 12 or more;

adding water after the addition of the first base to separate a carbonate precursor from the depolymerization reaction product; and adding an acid to adjust the pH of the depolymerization reaction product from which the carbonate precursor has been separated to be 2 or less, wherein the method further comprises a purification step of the depolymerization reaction product from which the carbonate precursor has been separated, and wherein the purification step comprises a recrystallization step, and an adsorption purification step.

5. The method for preparing a monomer composition according to claim 4, wherein in the step of adding the first base, an aromatic diol compound contained in the depolymerization reaction product is converted into a salt of the aromatic diol compound.

6. The method for preparing a monomer composition according to claim 4, wherein in the step of adding water, a water layer containing a salt of an aromatic diol compound and an organic solvent layer containing diethyl carbonate are separated.

7. The method for preparing a monomer composition according to claim 4, wherein in the step of adding the acid, a salt of an aromatic diol compound contained in the depolymerization reaction product is converted into the aromatic diol compound.

8. The method for preparing a monomer composition according to claim 4, wherein the depolymerization reaction of the polycarbonate-based resin is carried out in the presence of a solvent containing ethanol.

9. The method for preparing a monomer composition according to claim 8, wherein a content of the ethanol is 10 to 15 moles relative to 1 mole of the polycarbonate-based resin.

10. The method for preparing a monomer composition according to claim 4, wherein the depolymerization reaction of the polycarbonate-based resin is carried out by reacting a second base in an amount of 0.5 moles or less relative to 1 mole of the polycarbonate-based resin.

11. The method for preparing a monomer composition according to claim 4, wherein the purification step comprises:

a washing step for the depolymerization reaction product from which the carbonate precursor has been separated.

12. A recycled plastic, comprising:

a reaction product of the monomer composition of claim 1 and a comonomer.

13. A molded product, comprising:

the recycled plastic of claim 12.

\* \* \* \* \*